(12) United States Patent
Gumm (10) Patent No.: US 8,152,830 B2
(45) Date of Patent: Apr. 10, 2012

(54) ROTATING STENT DELIVERY SYSTEM FOR SIDE BRANCH ACCESS AND PROTECTION AND METHOD OF USING SAME

(75) Inventor: Darrel C. Gumm, Peoria, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 10 days.

(21) Appl. No.: 12/643,905

(22) Filed: Dec. 21, 2009

(65) Prior Publication Data

US 2010/0094250 A1    Apr. 15, 2010

Related U.S. Application Data

(63) Continuation of application No. 10/952,006, filed on Sep. 28, 2004, now Pat. No. 7,635,383.

(51) Int. Cl.
*A61M 29/00* (2006.01)
*A61M 31/00* (2006.01)
*A61F 2/06* (2006.01)

(52) U.S. Cl. ............ 606/194; 623/1.11; 604/96.01; 604/103.04

(58) Field of Classification Search ......... 600/434; 606/108, 194, 192, 193, 198, 195, 191; 604/101.04, 604/103, 103.03, 103.5, 161, 164.01, 164.13, 604/509, 510, 528, 96.01, 103.04, 93.01, 604/95.05, 102.01–102.03, 103.01, 103.06–103.14, 604/165.04, 166.01; 623/1.11, 1.35; 424/444, 424/426

See application file for complete search history.

(56) References Cited

U.S. PATENT DOCUMENTS

| | | | |
|---|---|---|---|
| 5,324,259 A | 6/1994 | Taylor et al. | |
| 5,397,305 A | 3/1995 | Kawula et al. | |
| 5,609,627 A | 3/1997 | Goicoechea et al. | |
| 5,749,825 A | 5/1998 | Fischell et al. | |
| 5,916,263 A | 6/1999 | Goicoechea et al. | |
| 5,968,068 A | 10/1999 | Dehdashtian et al. | |
| 6,099,497 A * | 8/2000 | Adams et al. ............ | 604/96.01 |
| 6,129,738 A | 10/2000 | Lashinski et al. | |
| 6,165,195 A * | 12/2000 | Wilson et al. ............ | 606/194 |
| 6,210,431 B1 | 4/2001 | Power | |
| 6,261,316 B1 | 7/2001 | Shaolian et al. | |
| 6,302,906 B1 | 10/2001 | Goicoechea et al. | |
| 6,383,213 B2 | 5/2002 | Wilson et al. | |
| 6,387,120 B2 | 5/2002 | Wilson et al. | |
| 6,540,719 B2 | 4/2003 | Bigus et al. | |
| 6,544,218 B1 | 4/2003 | Choi | |
| 2002/0072755 A1 | 6/2002 | Bigus et al. | |
| 2002/0077624 A1 * | 6/2002 | Lehmann et al. ............ | 606/21 |
| 2002/0099364 A1 | 7/2002 | Lalonde | |

(Continued)

FOREIGN PATENT DOCUMENTS

WO    03/017872    3/2003

(Continued)

*Primary Examiner* — S. Thomas Hughes
*Assistant Examiner* — Jocelin Tanner
(74) *Attorney, Agent, or Firm* — Seager, Tufte & Wickhem, LLC (57) ABSTRACT

A system for treatment of a vessel bifurcation and its method of use comprises a catheter having a catheter shaft, a portion of which is characterized as an axle about which a rotatable assembly is disposed and rotatable thereabout. The system employs a series of lumens, openings and/or ports to provide a balloon mounted on the rotatable assembly with fluid communication to the catheter shaft.

18 Claims, 9 Drawing Sheets

U.S. PATENT DOCUMENTS

| | | | |
|---|---|---|---|
| 2003/0028234 A1* | 2/2003 | Miller et al. | 623/1.11 |
| 2003/0055483 A1* | 3/2003 | Gumm | 623/1.11 |
| 2004/0172119 A1 | 9/2004 | Eidenschink | |
| 2004/0172121 A1* | 9/2004 | Eidenschink et al. | 623/1.11 |
| 2004/0254528 A1* | 12/2004 | Adams et al. | 604/96.01 |
| 2005/0149161 A1 | 7/2005 | Eidenschink et al. | |
| 2005/0154442 A1 | 7/2005 | Eidenschink et al. | |
| 2005/0183259 A1 | 8/2005 | Eidenschink et al. | |
| 2005/0187602 A1 | 8/2005 | Eidenschink | |

FOREIGN PATENT DOCUMENTS

| | | |
|---|---|---|
| WO | 2004/075792 | 9/2004 |

\* cited by examiner

ROTATING STENT DELIVERY SYSTEM FOR SIDE BRANCH ACCESS AND PROTECTION AND METHOD OF USING SAME

This application is a continuation of U.S. application Ser. No. 10/952,006, filed on Sep. 28, 2004, entitled "ROTATING STENT DELIVERY SYSTEM FOR SIDE BRANCH ACCESS AND PROTECTION AND METHOD OF USING", which is hereby incorporated by reference.

STATEMENT REGARDING FEDERALLY SPONSORED RESEARCH

Not Applicable

BACKGROUND OF THE INVENTION

1. Field of the Invention

At least one embodiment of the present invention is directed to the field of stents and stent delivery systems used to treat stenoses, and more particularly to stenoses at a bifurcation of a passage and/or ostium of vessel.

2. Description of the Related Art

Stent systems are widely used in the treatment of stenoses. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

It is recognized, however, that a stent can be deployed in manners other than inflating and deflating a balloon. For example, self-expanding stents have been developed in which a cover is removed from over a stent, thereby allowing the stent to deploy or spring into place. It is also contemplated that other deployment mechanisms or means may be used or developed to advantageously deliver and deploy a stent in position.

Nevertheless, a need still exists for properly delivering and locating a stent at a bifurcation. Although efforts have been made to use a stent at bifurcations, these sites have previously been inadequately treated by a stent. For example, U.S. Pat. No. 5,749,825 is representative of a catheter system that treats stenoses at an arterial bifurcation. The disclosure of U.S. Pat. No. 5,749,825 is hereby incorporated by reference.

A stent having different diameters has been proposed to allow placement in both a main passage, such as an artery, and a side branch passage, such as a continuation branch artery. Additionally, these stents generally have a circular opening which allows for unimpeded blood flow into the side branch artery. However, problems are still encountered in orienting the stent relative to the side branch at the bifurcation of the main and branch passages.

Many current devices rely on the application of torque from outside of the patient to properly orient the stent delivery system in the passage. These devices and methods of achieving proper angular orientation have not been shown to be effective in properly placing and positioning the stent. As will be appreciated and understood by those skilled in the art, improper placement of the stent with respect to its rotational or circumferential orientation, or its longitudinal placement, could lead to obstruction of the side branch passage. It is important to properly position or center an opening formed in the bifurcated stent with the side branch passage to maximize flow therethrough.

Thus, a need exists for effectively treating stenosed passage bifurcations. This need includes more precise and exact longitudinal placement and rotational/circumferential orientation of the stent.

Commercially available devices do not maintain side branch access at the time of stent deployment. This results in the potential for plaque shift and occlusion of the side branch passage.

It would also be advantageous if stents could be placed across the side branch while wire position is maintained thereby helping to protect and secure further access to the side branch. All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention contemplates a new and improved apparatus and method that improves the orientation of a stent by providing a more exact placement of the stent relative to the side branch passage of a bifurcation. This, in turn, leads to better protection of the side branch passage. The present invention has the potential for improvement in trackability of the stent delivery system.

Catheter systems for delivery of multiple stents or stent segments, wherein at least one of the stents is mounted on a catheter having a rotational section are described in U.S. patent application Ser. No. 10/226,362, filed Aug. 22, 2002 and entitled Rotating Stent Delivery System for Side Branch Access and Protection and Method of Using the Same. Medical devices employing catheters having alternate rotatable mechanisms and methods for stent delivery are also described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; U.S. patent application Ser. No. 10/757,646, filed Jan. 13, 2004 and entitled Bifurcated Stent Delivery System; and U.S. patent application Ser. No. 10/784,337, filed Feb. 23, 2004 and entitled Apparatus and Method for Crimping a Stent Assembly; the entire content of each of the above being incorporated herein by reference.

In the present invention some embodiments are directed to such catheter systems wherein a catheter employs a rotatable assembly disposed about a portion of the catheter shaft. The rotatable assembly comprises a rotatable member or barrel defining a hollow rotation passage through which the portion of the catheter shaft (e.g. an "axle portion") about which the barrel rotates is positioned. The barrel further defines one or more external fluid ports in fluid communication with the rotation passage. The catheter shaft defines an inflation lumen which is in fluid communication with the rotation passage and thus the fluid ports of the barrel.

In some embodiments an expandable medical balloon is engaged externally to the barrel. By way of the fluid ports the interior of the balloon is in fluid communication with the inflation lumen of the catheter shaft. As a result, the balloon is fluid expandable via transmission of an inflation fluid and/or contrast agent through the inflation lumen.

In order to facilitate ease of rotation of the barrel about the axle portion of the catheter shaft a gap or space may be present between the catheter (shaft) and the barrel. In at least one embodiment the balloon defines a pair of end overlapping portions which are constructed and arranged to form a seal between the barrel and the catheter during expansion of the balloon. Such overlapping portions act to prevent or limit leakage of inflation fluid from the assembly and/or catheter through the gap(s).

In at least one embodiment the rotational assembly includes one or more flaps or negative pressure seal membranes which extend from the barrel to the catheter to form a fluid tight seal over the gaps during application of negative pressure to the balloon following expansion.

In at least one embodiment the catheter shaft further defines a primary guidewire lumen for passage of a primary guidewire therethrough. Typically, the catheter is advanced through a body lumen, such as a blood vessel or artery along the primary guidewire. Rotation may be imparted to the rotatable assembly through the use of a secondary guidewire slideably engaged directly or indirectly to the barrel.

In at least one embodiment a secondary guidewire housing is engaged to a portion of the balloon mounted to the barrel. The secondary guidewire housing defines a secondary guidewire lumen for passage of the secondary guidewire therethrough. Typically, the secondary guidewire will run along side the primary guidewire through the vessel until the secondary guidewire diverges into a branch vessel at a vessel bifurcation. By advancing the catheter simultaneously along both wires the catheter may advanced to the vessel bifurcation and the balloon properly positioned. The secondary guidewire, via the secondary guidewire housing, will act to impart rotation to the barrel independent of the catheter shaft to align the balloon in the proper rotational position at the bifurcation. This feature is particularly useful where the catheter is utilized to deliver a stent or other implantable device at or adjacent to the bifurcation.

In at least one embodiment a stent or other implantable device is disposed about the balloon in a reduced diameter configuration. When the balloon is expanded the stent is deployed. In the reduced state, at least a portion of the secondary guidewire housing underlies the stent to allow the secondary guidewire to effectively pass under a portion of the stent and out one of the openings in the wall of the stent. Such a configuration allows a first portion of the stent to be deployed in the primary vessel distal of the branch vessel and a second portion of the stent to be deployed proximal of the branch vessel. The stent opening through which the secondary guidewire passes maintains a side-branch opening therebetween.

In some embodiments the secondary guidewire passes through the entire length of the stent, extending from the proximal to the distal end of the stent. In other embodiments the secondary guidewire passes through the side of the stent and/or adjacent the proximal edge of the stent.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
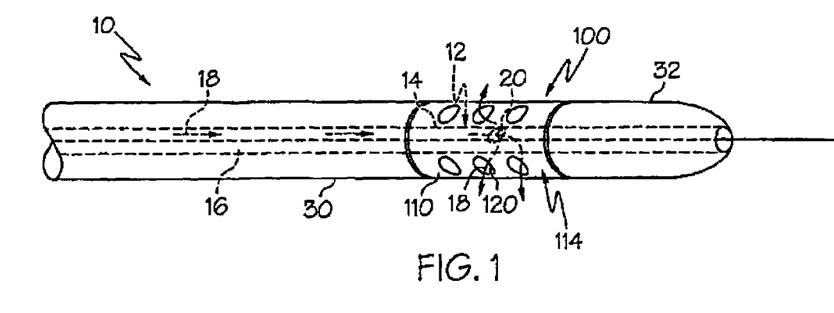
FIG. 1 is a partial perspective view of an embodiment of the invention comprising a catheter having a rotatable assembly.

In at least one embodiment of the invention, an example which is illustrated in FIG. 1 a catheter 10 is shown having a rotational assembly 100. The rotational assembly 100, shown free of the catheter in FIG. 3, is independently rotatable about a portion of the catheter shaft 12, referred to hereinafter as an axle or axle portion 14, such as is shown in FIG. 2.

Figure 2:
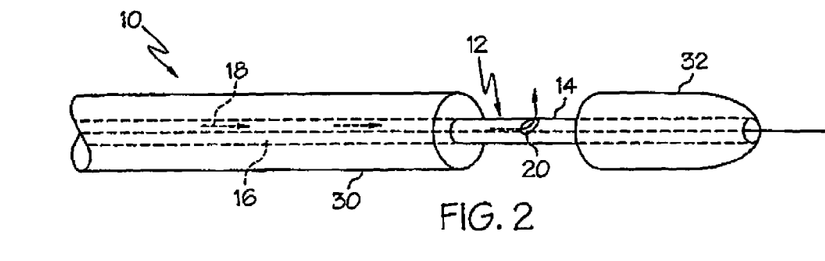
FIG. 2 is a perspective view of the embodiment shown in FIG. 2, depicted with the rotatable assembly removed from the catheter shaft.

As depicted in FIG. 2 the catheter shaft 12 defines an inflation lumen 16 through which an inflation fluid, depicted as arrows 18, may be passed therethrough. A portion of the axle 14 defines an axle fluid port 20, through which the fluid 18 may exit the inflation lumen 16 under the rotational assembly 100, as in the manner depicted in FIG. 3.

Figure 3:
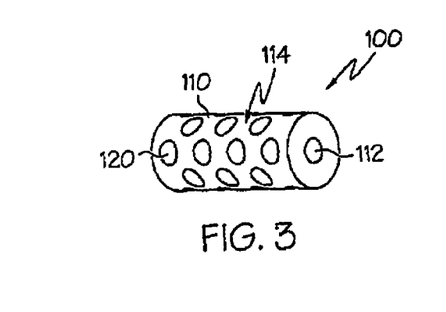
FIG. 3 is a perspective view of the rotatable assembly of FIG. 1 shown separated from the catheter shaft.
Figure 6:
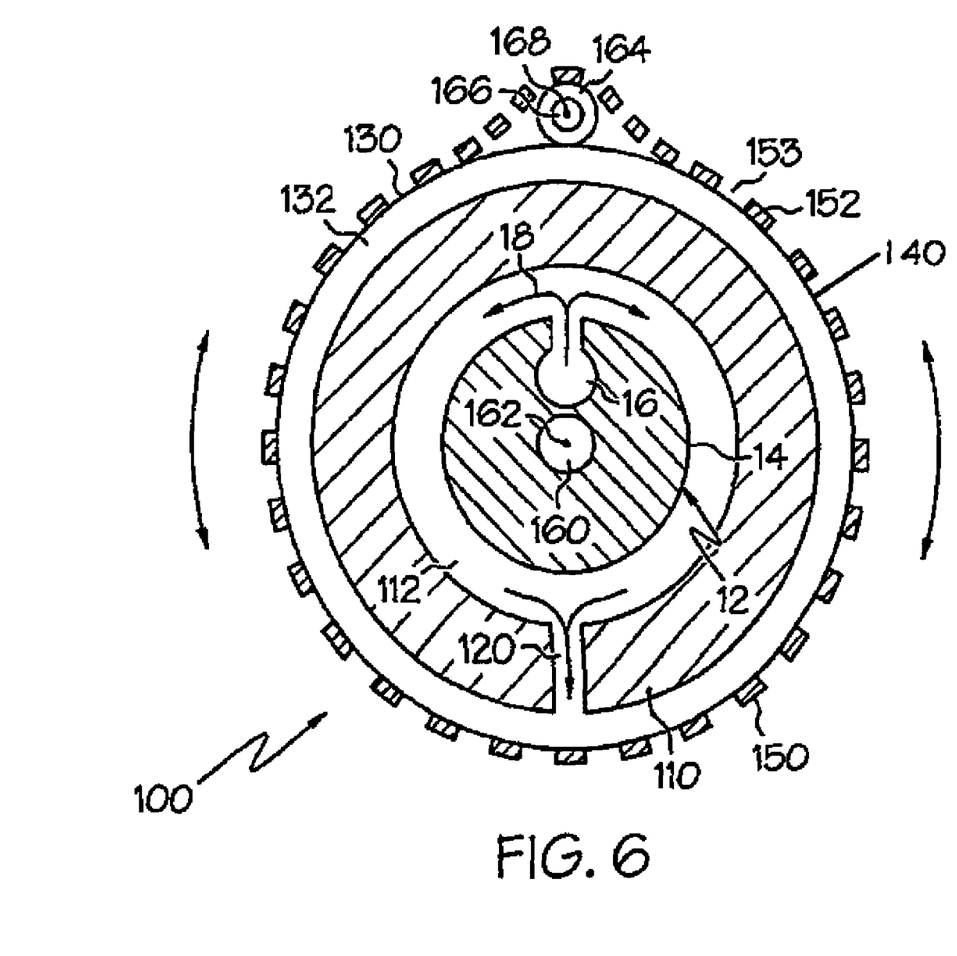
FIG. 6 is a cross-sectional view of the embodiment shown in FIG. 5.

As shown in FIG. 3, the rotational assembly 100 comprises a rotation member or barrel 110. Barrel 110 defines a substantially hollow rotation passage or 'inside' 112 through which the axle portion 14 of the catheter shaft 12 is positioned. As is illustrated in FIG. 6 because the passage 112 has a diameter greater than that of the diameter of the axle 14, the barrel 110, and thus the entire rotational assembly 100, is rotatable thereabout.

The barrel 110 further defines one or more barrel fluid ports 120 which provide fluid communication between the rotation passage 112 and the external surface or 'outside' 114 of the barrel 110. By way of the proximity of the axle fluid port 20 and the rotation passage 112 it should be apparent that when the rotational assembly 100 is disposed about the axle 14, a fluid path becomes available to allow fluid 18 injected into the inflation lumen 16 to pass through the lumen 16, out the axle fluid port 20, into the rotation passage 112 of the barrel 110, and through the barrel fluid ports 120, such as in the manner depicted in FIGS. 1 and 6.

Figure 4:
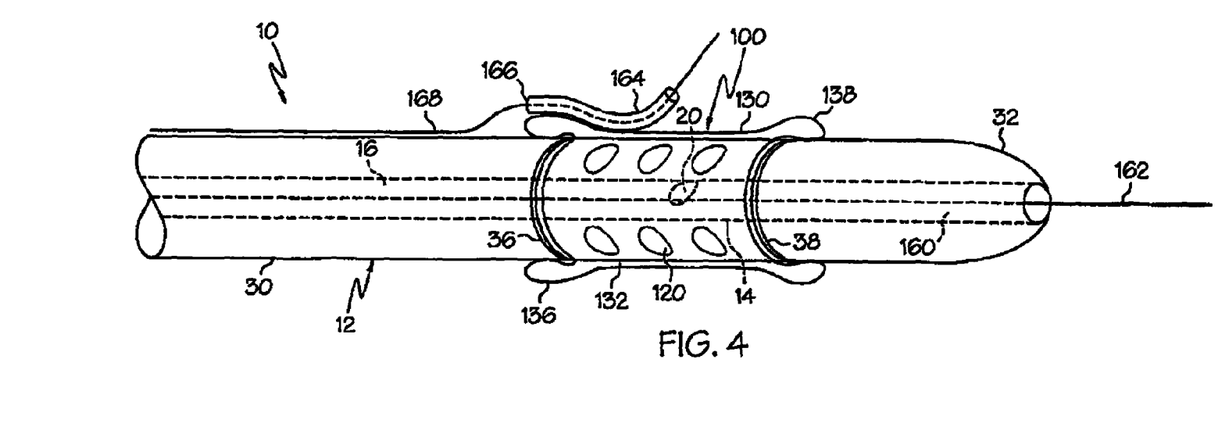
FIG. 4 is a perspective view of the embodiment depicted in FIG. 1 wherein the rotatable assembly further comprises an expandable balloon and secondary guidewire housing.

In some embodiments, an example of which is shown in FIG. 4 the rotational assembly 100 further comprises an expandable medical balloon 130 which is sealingly engaged to and about at least a portion of the barrel 110, such that the balloon interior 132 is in fluid communication with the barrel fluid ports 120. As a result of this relationship, fluid 18 may be directed into the balloon 130 and may be utilized to expand the balloon 130 from an unexpanded state to an expanded state wherein the diameter or size of the balloon is increased by fluid inflation.

As is shown in FIGS. 1 and 4, the catheter 10 may comprise regions proximal and distal to the axle 14 which have respective diameters greater than that of the rotational passage 112.

Such a proximal region 30 and distal region 32 maybe comprised of any of a variety of catheter components, such as portions of the catheter housing, external shaft(s) hubs, retaining collars, tip, etc. In the embodiment shown in FIG. 1, regions 30 and 32 are characterized as portions of the catheter shaft 12 having diameters greater than that of the axle 14 and the rotation passage 112. Regions 30 and 32 are spaced longitudinally apart a distance sufficient to allow the rotational assembly 100 to be positioned therebetween without significantly interfering with the rotatablility of the assembly 100 relative to the catheter 10, while simultaneously limiting and/or preventing significant longitudinal movement of the assembly 100 relative to the catheter shaft 12. As shown in FIG. 1, in some embodiments, the distance between the regions 30 and 32 is at least slightly greater than the length of the barrel 110. As a result, there may be present a proximal gap 36 between the proximal region 30 of the shaft 12 and the barrel 110, and a distal gap 38 between the distal region 32 of the shaft 12 and the barrel 110.

While the presence of gaps 36 and 38 reduce the potential for frictional interference between the assembly 100 and catheter 10, the gaps also provide a path through which fluid 18 may flow, particularly during expansion of the balloon 130 under pressure. To prevent or reduce such fluid flow, in at least one embodiment of the invention the balloon 130 comprises a proximal overlap 136 and a distal overlap 138 which act to provide a fluid seal about the gaps 36 and 38 during balloon expansion.

Proximal overlap 136 is a portion of the balloon 130 that extends proximally from the rotational assembly 100, over and about the proximal gap 36 and at least a portion of the proximal region 30 of the catheter shaft 12 immediately adjacent to the gap 36. Likewise, distal overlap 138 is a portion of the balloon 130 that extends distally from the rotational assembly 100, over and about the distal gap 38 and at least a portion of the distal region 32 of the catheter shaft 12 immediately adjacent to the gap 38.

Figure 4A:
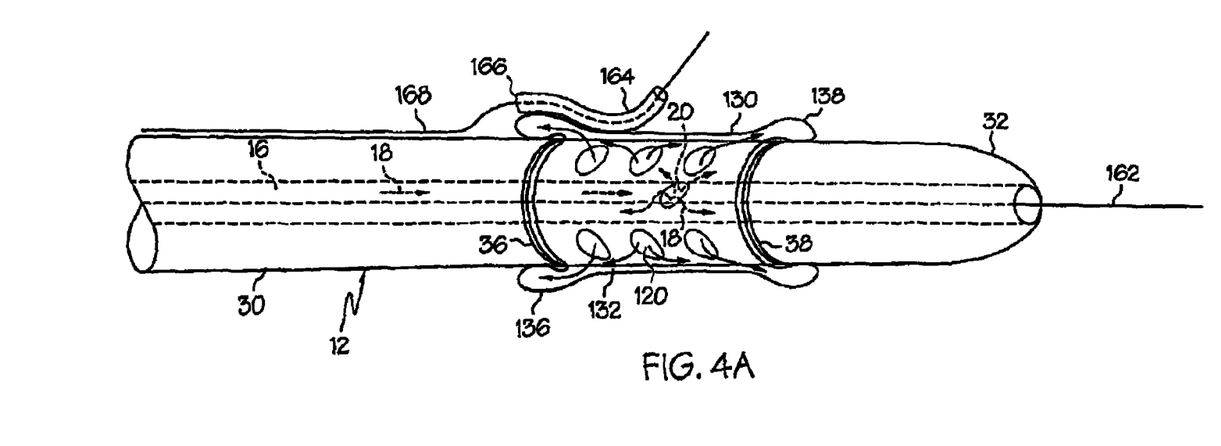
FIG. 4a is a partial enlarged view of the embodiment depicted in FIG. 4 shown during initial balloon expansion.

As illustrated in FIG. 4a, when fluid 18 is passed into the balloon 130 in the manner previously described, the initial expansion of the balloon 130 will tend to push the overlaps 136 and 138 radially inward to engage the respective regions 30 and 32 of the catheter shaft 12 adjacent thereto. As a result the balloon 130 via the overlaps 136 and 138 forms a fluid tight seal with the catheter shaft 12 to prevent fluid loss through the gaps 36 and 38.

Figure 4B:
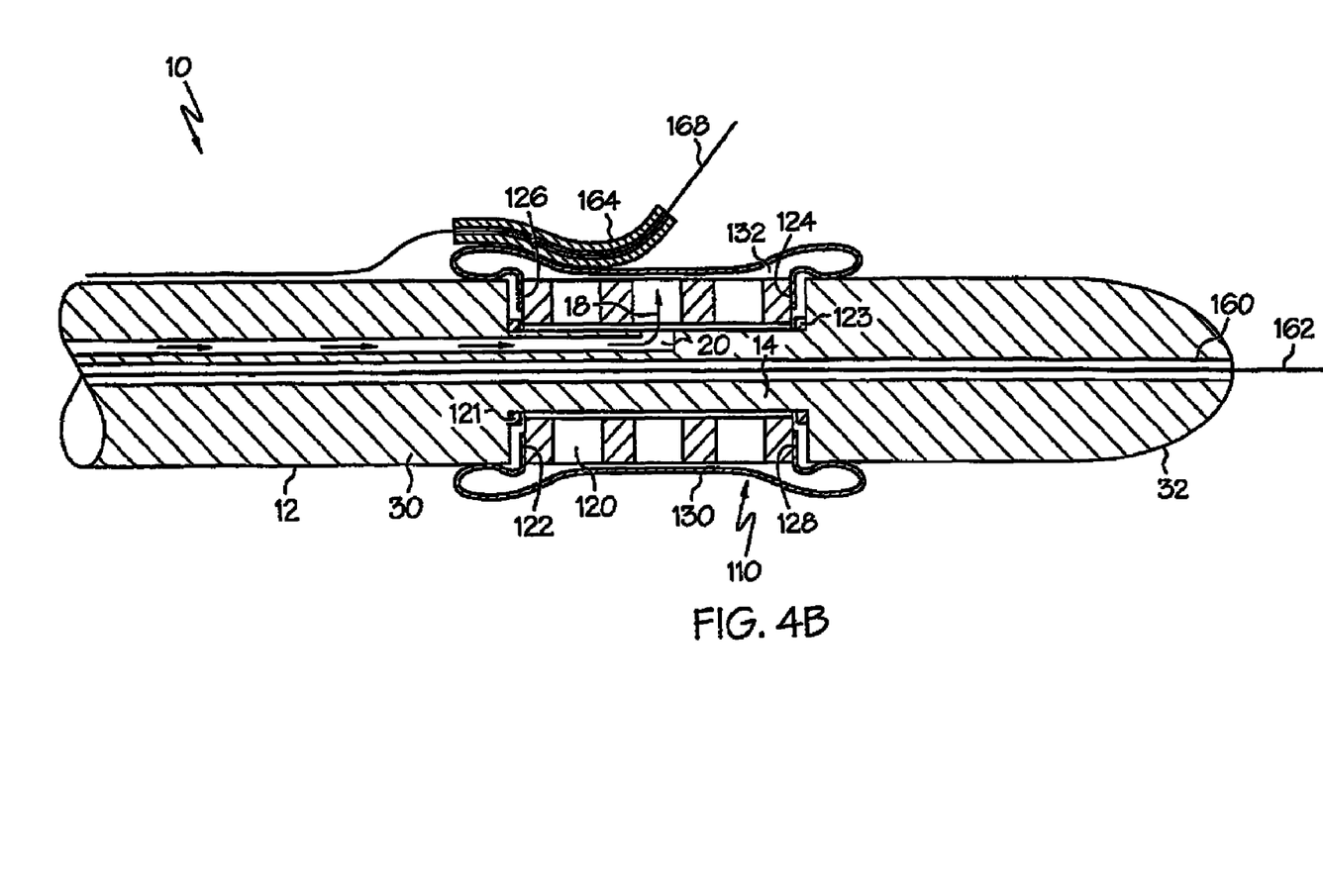
FIG. 4b is a partial enlarged side-view of the embodiment depicted in FIG. 4 wherein the balloon is engaged to the lateral surfaces of the barrel.

In some embodiments the rotatable assembly 100 may be provided with a variety of mechanisms to reduce or prevent loss of fluid 18 through the gaps 36 and 38. For example in the embodiment illustrated in FIG. 4b each waist 122 and 124 of the balloon 130 is respectively engaged to a lateral surface 126 and 128 of the barrel 110. Such a configuration allows the proximal waist 122 to act as a flexible gasket between the proximal surface 126 of the barrel 110 and the proximal region 30 of the catheter shaft 12. Likewise the distal waist 124 acts as a flexible gasket between the distal surface 128 of the barrel 110 and the distal region 32 of the catheter shaft 12. The balloon waists 122 and 124 maybe provided with any desired thickness so as to properly seal the respective gaps 36 and 38 without significantly affecting the rotatablility of the assembly 100.

In some embodiments one or more gaskets, seals, valves or other sealing mechanisms 121 and 123 may be positioned within or adjacent to the gaps 36 and 38 independent of the balloon 130 to provide an additional or alternative fluid seal.

Figure 5:
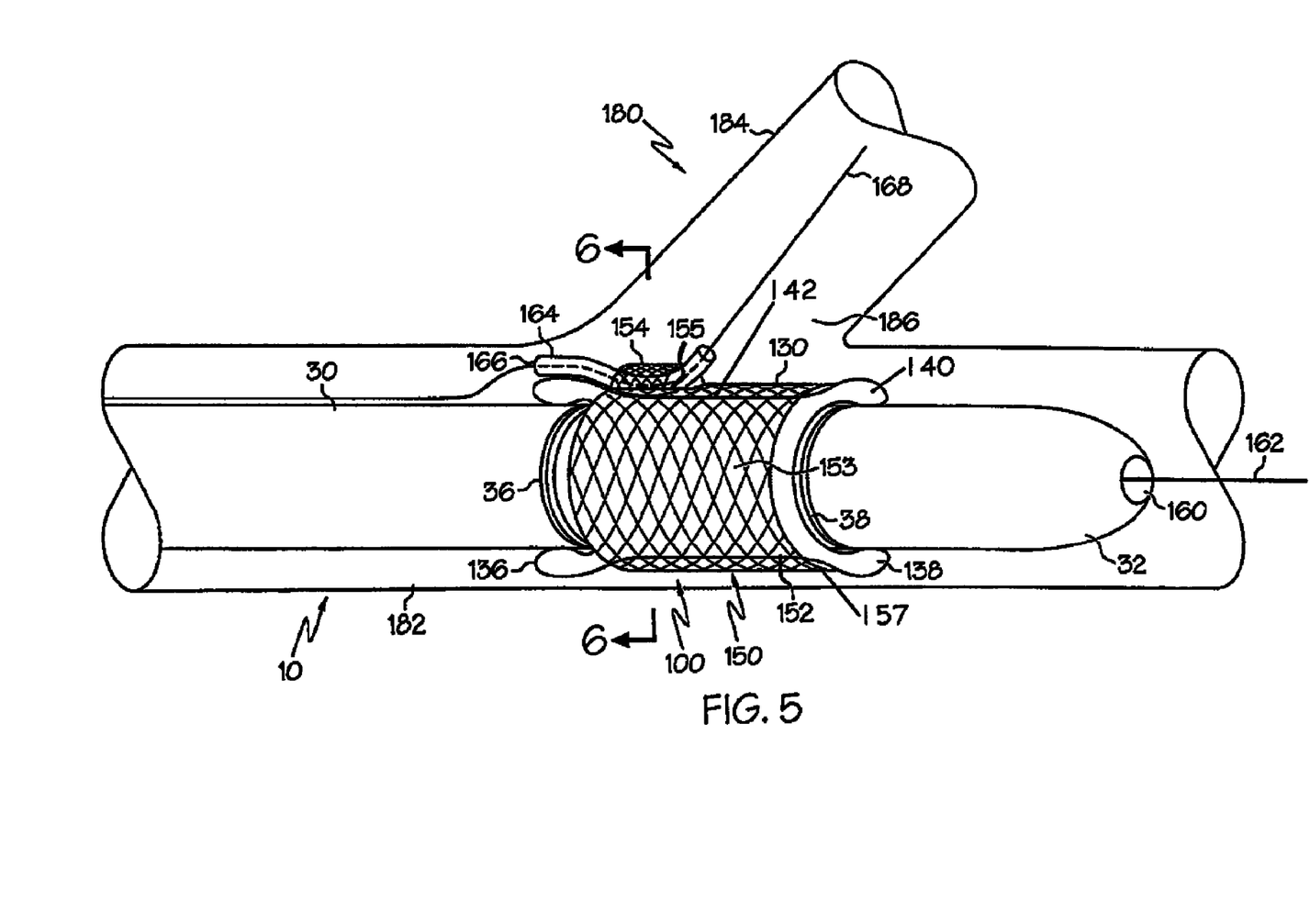
FIG. 5 is a perspective view of the embodiment depicted in FIG. 4 wherein a stent in the reduced diameter state is disposed about the rotatable assembly and is shown being advanced to a vessel bifurcation.

Returning to the embodiment illustrated in FIG. 4a, the tendency for the overlaps 136 and 138 to push against the shaft 12 is particularly pronounced when the body 140 of the balloon 130 (the body 140 being defined as the portion of the balloon 130 between the overlaps 136 and 138) is constrained and the overlaps 136 and 138 are unconstrained, such as for example when a stent 150 or other medical device, such as is shown in FIG. 5, is disposed about the balloon body 140 prior to expansion.

As used herein the term 'stent' refers to an expandable prosthesis for implantation into a body lumen or vessel and includes devices such as stents, grafts, stent-grafts, vena cava filters, expandable frameworks, etc. In some embodiments a stent may be at least partially constructed of any of a variety of materials such as stainless steel, nickel, titanium, nitinol, platinum, gold, chrome, cobalt, as well as any other metals and their combinations or alloys. In some embodiments a stent may be at least partially constructed of a polymer material. In some embodiments a stent may be at least partially constructed of a shape-memory polymer or material. In some embodiments a stent may be balloon expandable, self-expandable, hybrid expandable or a combination thereof. In some embodiments a stent may include one or more radiopaque members. In some embodiments a stent or other portions of the catheter and/or assembly may include one or more therapeutic and/or lubricious coatings applied thereto.

In some embodiments stent 150, catheter 10 and/or rotatable assembly 100 may include one or more areas, bands, coatings, members, etc. that is (are) detectable by imaging modalities such as X-Ray, MRI or ultrasound. In some embodiments at least a portion of the stent 150, catheter 10 and/or rotatable assembly 100 is at least partially radiopaque. In some embodiments the stent 150, catheter 10 and/or rotatable assembly 100 may include one or more therapeutic and/or lubricious coatings applied thereto.

As illustrated in FIG. 5, at least a portion of the body 140 of the balloon 130 defines a stent receiving region 142 about which a stent 150 in the reduced diameter configuration is mounted. Prior to delivery, stent 150 may be engaged to the stent receiving region 142 by any mechanism or method known or desired. Once the catheter 10 is advanced to a desired location in a body vessel the balloon 130 is inflated by fluid 18 in the manner previously described and the stent 150 is correspondingly expanded from the reduced configuration to an expanded or delivered configuration. In the expanded configuration the diameter of the stent is greater than that in the unexpanded configuration.

While the embodiment depicted in FIG. 5 employs a balloon 130 to deploy the stent 150, it is recognized that embodiments of the invention may be utilized which do not require the use or presence of the balloon. In such an instance, a self-expanding stent may be disposed about the barrel 110 employing the appropriate retaining and delivery mechanisms.

While it is clear that the stent 150 may be any type of stent, including a rolled sheet stent, a wire stent, a coil stent or a cut-tube stent, for purposes of description the stent 150 shown in FIG. 5 is characterized as comprising a plurality of interconnected struts or stent members 152 which define a plurality of stent openings 153. At least one of the openings 153 is designated as a side-branch opening 155. The side branch opening refers to that opening of the stent which is configured to be aligned with the ostium of a side branch vessel at a bifurcation, and through which a secondary guidewire 168 and/or subsequent catheter assemblies may be passed.

As is discussed in greater detail below, it should be recognized however that the positioning of the stent 150 relative to the ostium of the branch vessel may be varied depending on where the side-branch opening 155 is located along the length of the stent. Alternatively, the entire stent may be accurately positioned adjacent the side branch vessel opening by configuring the system such that the secondary guidewire 168 is proximally or distally adjacent to the stent.

As mentioned previously, the rotatable assembly 100 is rotatable about the axle 14 of the catheter shaft 12. The degree of rotation and its direction may be controlled through the use of divergent first and second guidewires 162 and 168 upon which the catheter 10 and rotational assembly 100 are respectively advanced simultaneously.

In the embodiment depicted in FIGS. 5 and 6 for example, the catheter shaft 12 further defines a first or primary guidewire lumen 160 through which the first guidewire 162 is passed. In use the catheter 10 is advanced along the first guidewire 162 to a predetermined location in a body vessel, such as a vessel bifurcation. It should be noted however that in some embodiments the catheter 10 may be configured as a fixed wire catheter.

A secondary guidewire housing 164 is engaged to the balloon 130 or other portion of the rotational assembly 100. The secondary guidewire housing 164 defines a secondary guidewire lumen 166 through which the secondary guidewire 168 is passed. As the catheter 10 is advanced along the first guidewire 162 the secondary guidewire housing 164 is advanced along the secondary guidewire 168. As the catheter 10 approaches a vessel bifurcation 180, such as is shown in FIG. 5, the secondary guidewire housing 168, and thus the entire rotational assembly 100, is rotated as directed by the divergence of the secondary guidewire 168 from the first guidewire 162 where it advances into the side branch vessel 184.

In at least one embodiment, an example of which is shown in FIG. 5, at least a portion of the secondary guidewire housing 164 (and thus, the secondary guidewire 168 positioned therein) underlies a proximal portion 154 of the stent 150. By allowing the secondary guidewire to "exit" the stent 150 through the side-branch opening 155 allows the side-branch opening 155 of the stent 150 to in effect automatically align itself with the ostium 186 of the branch vessel 184, thereby providing a continuous flow path between the primary vessel 182 and the side-branch vessel 184. In at least one embodiment the side-branch opening 155 of the stent 150 is about 2 mm from the distal edge of the stent 150.

Figure 8:
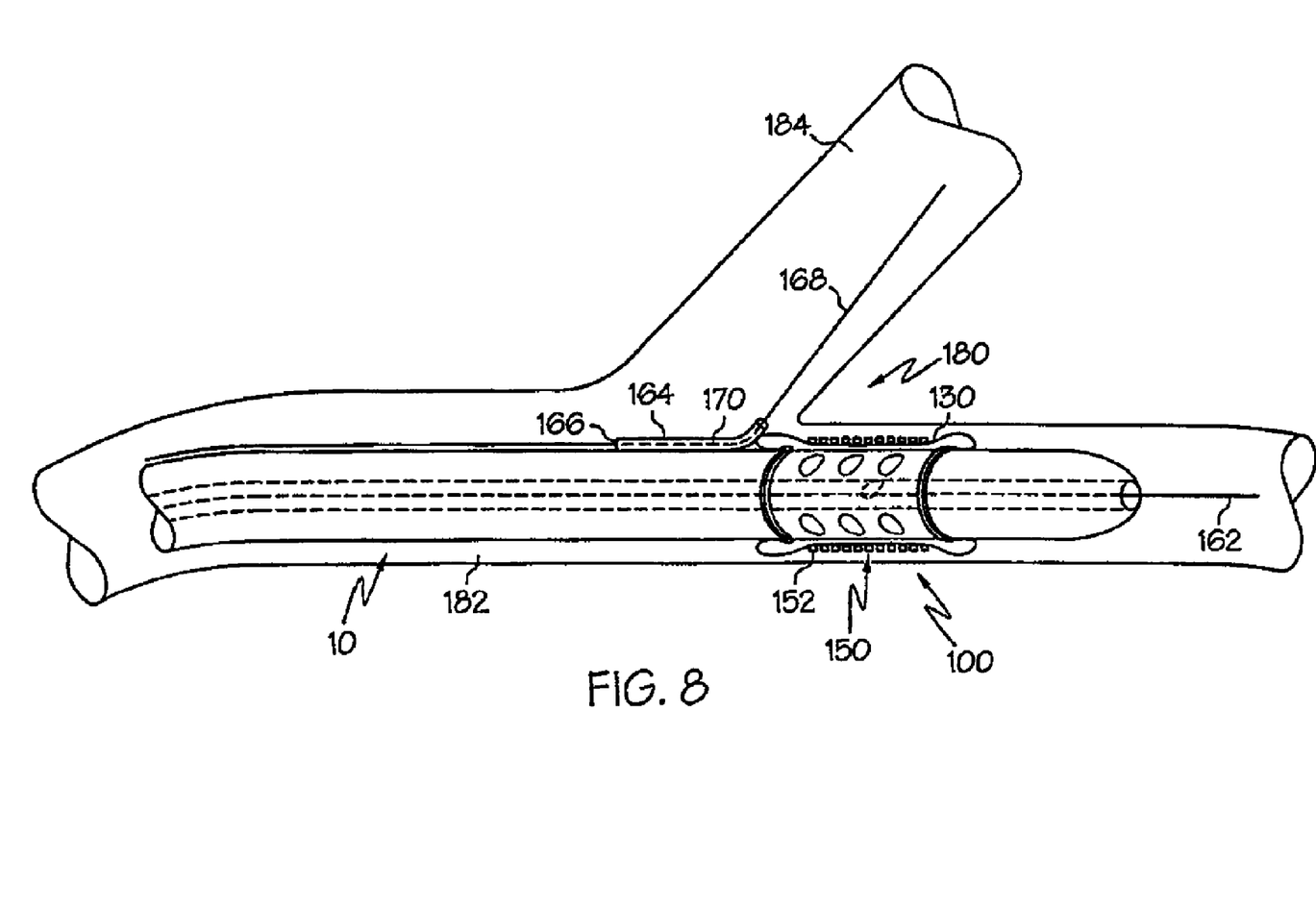
FIG. 8 is a side perspective view of an embodiment of the invention, wherein the assembly is provided with a frangible secondary guidewire housing adjacent to the stent.

Alternatively, the secondary guidewire housing 164 can be positioned such that the secondary guidewire 168 does not pass under or through the stent 150, but rather is proximally or distally adjacent to thereto, such as in the manner illustrated in FIG. 8. Such a configuration allows the stent 150 to be accurately positioned on one side or the other of the ostium of the branch vessel as desired.

In some embodiments, such as that which is seen in FIG. 5, once the stent 150 is positioned at the vessel bifurcation 180, the balloon 130 is inflated and the stent 150 is expanded and delivered into the primary vessel 182, such that a distal portion 152 of the stent 150 is positioned distally adjacent to the side-branch vessel 184 and a proximal portion 154 of the stent 150 positioned proximally adjacent to the side-branch vessel 184. Where the assembly 100 provides for the placement of the stent 150 distally adjacent to the secondary guidewire housing 164, such as in the manner shown in FIG. 8, the entire stent 150 is deployed distally of the branch vessel.

Subsequent to the placement of the stent 150, one or more additional medical devices maybe advanced along one or both guidewires 162 and 168 for further treatment of the vessel(s) and or delivery of additional devices therein.

In at least one embodiment, an example of which is shown in FIG. 8, the secondary guidewire housing 164 defines a seam 170 or other feature which allows the secondary guidewire 168 to be freed from the lumen 166 of the housing 164 following delivery of the stent 150.

Mechanisms for allowing the housing 164 to "fail" in this manner may be provided by incorporating a bio-absorbable material into the construction of the housing 164; manufacturing the housing at least partially from shape memory material wherein the housing has a pre-programmed shape such that the housing 164 opens or unrolls along its length to allow the secondary guidewire 168 to escape the lumen 166; providing the housing 164 with a weakened or thinned region which is itself bio-absorbable or frangible by manipulation of the guidewire 168 or by application of an external mechanism such as an electromagnetic signal, ultrasound, etc.

In some embodiments the housing 164 may be defined by at least a portion of the balloon 130 (folds, etc.), the sheath 110, or other portions of the assembly 100.

Figure 9:
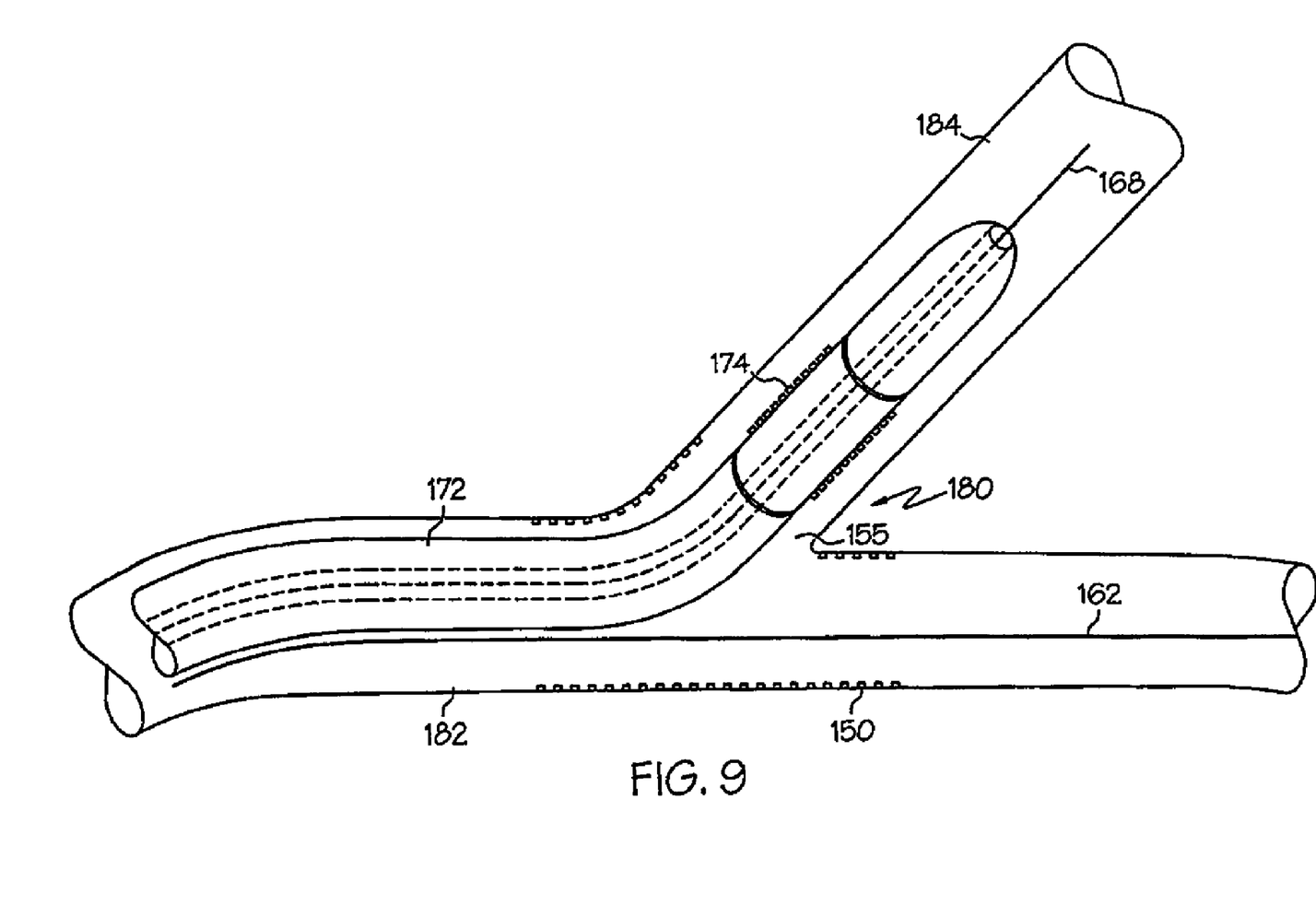
FIG. 9 is a side view of a stent, such as is depicted in FIG. 5, shown deployed across a vessel bifurcation and a secondary catheter is being advanced through the secondary opening of the stent.
Figure 10:
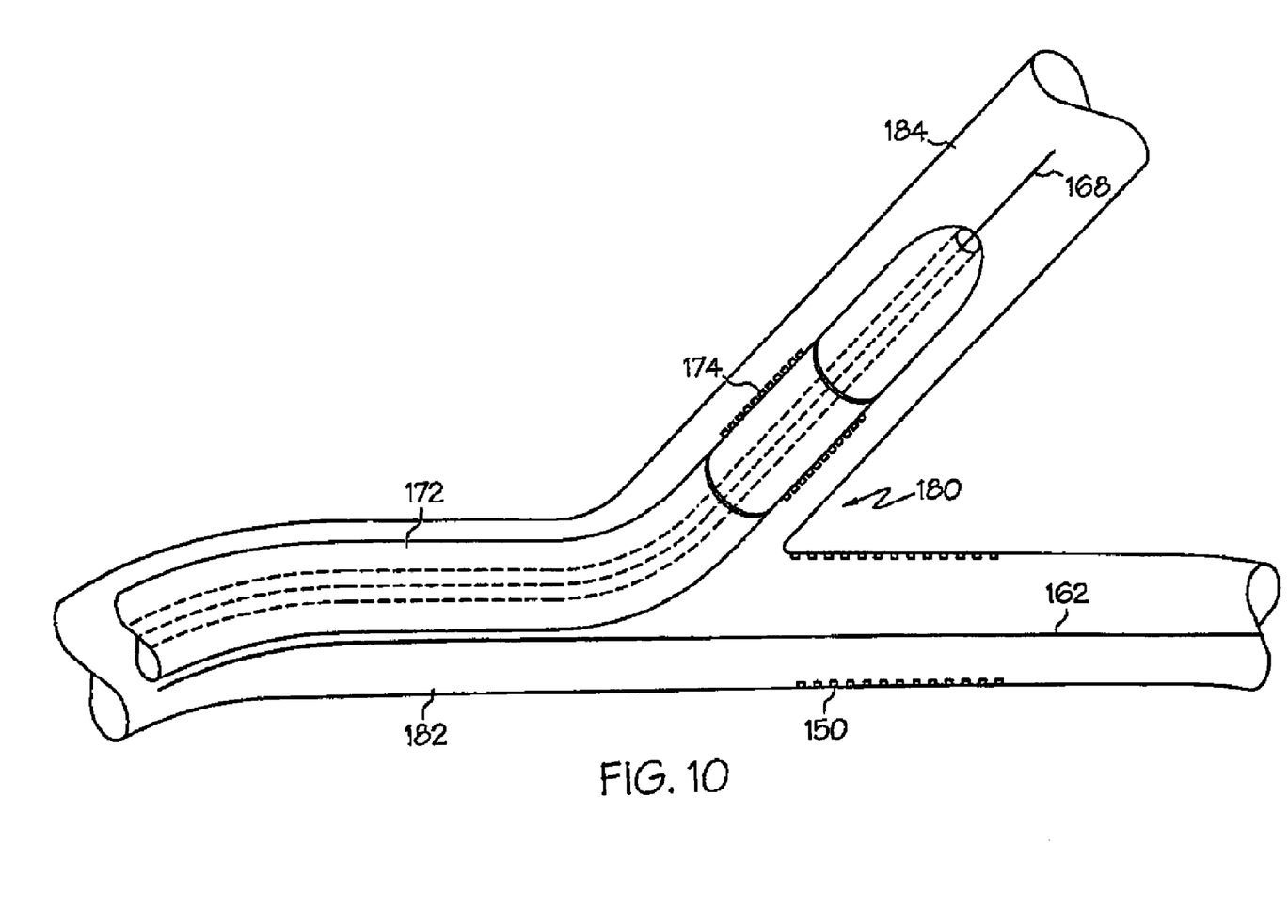
FIG. 10 is a side view of the stent depicted in FIG. 8 shown deployed adjacent to a side branch vessel at a bifurcation and a secondary catheter is being advanced into the side branch vessel.

Once the secondary guidewire 168 is free from the system, a second catheter, such as the second catheter 172 shown in FIG. 9, may be advanced along the secondary guidewire 168 so that a second stent 174 can be placed within the branch vessel 184 through the secondary opening 155 of the first stent 15, or in some embodiments, adjacent to the first stent 150, such as is shown in FIG. 10, depending on the position and placement of the first stent 150 at the bifurcation. Additional stents maybe advanced along one or both of the primary and secondary guidewires and positioned at or adjacent to the bifurcation as desired.

Returning to the embodiment depicted in FIG. 5, following delivery of the stent 150, the balloon 130 will be evacuated by application of negative pressure through the inflation lumen 16. In some embodiments where the overlaps 136 and 138 are not configured to remain sealed over the gaps 36 and 38 during deflation, the rotational assembly 100 may further comprise one or more negative pressure flaps 190 and 192, such as are shown in FIG. 7, which are configured to provide a fluid tight seal over the gaps 36 and 38 during deflation of the balloon 130.

Figure 7:
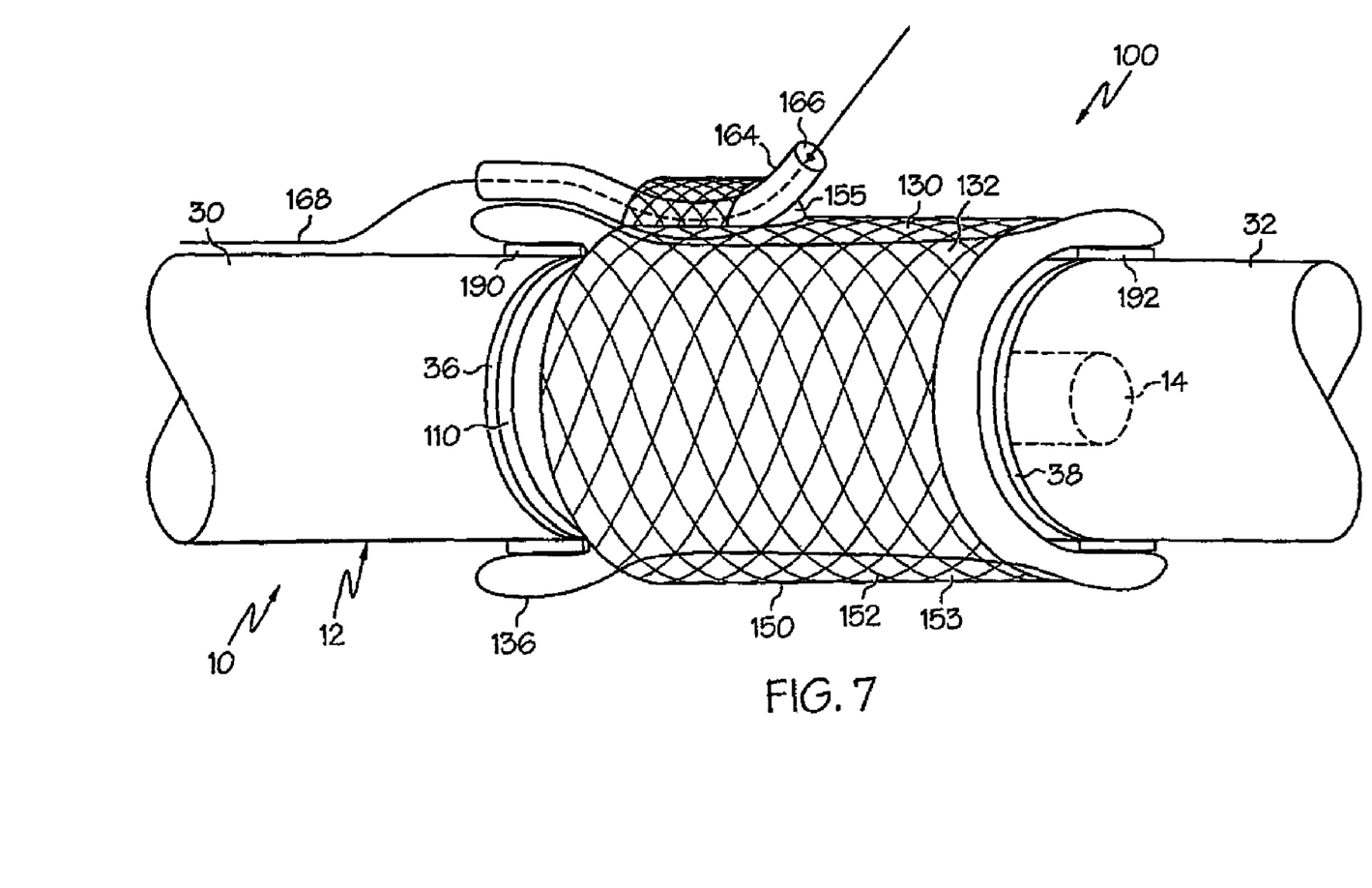
FIG. 7 is an enlarged partial perspective view of a portion of the embodiment depicted in FIG. 4 wherein the rotatable assembly further comprises a pair of sealing membranes.

As shown in FIG. 7, proximal flap 190 extends proximally from the barrel 110, over and about the proximal gap 36 and at least a portion of the proximal region 30 of the catheter shaft 12 immediately adjacent to the gap 36. Likewise, distal flap 192 extends distally from the barrel 110, over and about the distal gap 38 and at least a portion of the distal region 32 of the catheter shaft 12 immediately adjacent to the gap 38. When negative pressure is applied to the balloon 130 during deflation, the flaps 190 and 192 are drawn radially inward toward the shaft 14 to seal the gaps 36 and 38 respectively.

Flaps 190 and 192 may be constructed of any material suitable for providing a fluid tight seal. In at least one embodiment flaps 190 and 192 are at least partially constructed of PET. As indicated above, in the various embodiments of the invention at least a portion of the stent, catheter and/or rotatable assembly may include a coating of one or more therapeutic agents. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic includes cellular material, the cellular material may include but is not limited to: cells of human origin and/or non-human origin as well as their respective components and/or derivatives thereof. Where the therapeutic agent includes a polymer agent, the agent may be a polystyrene-polyisobutylene-polystyrene triblock copolymer (SIBS), polyethylene oxide, silicone rubber and/or any other suitable substrate.

The invention has been described with reference to the preferred embodiments. Obviously, modifications and alterations will occur to others upon a reading and understanding of this specification. For example, the illustrated embodiments use a balloon to expand the stent although, as briefly noted above, a self expanding or self deploying stent can be used without departing from the features of the present invention. Likewise, using a fixed wire on the distal end of the apparatus is also recognized as being consistent with the features of the present invention. Moreover, the preferred embodiments describe various components such as a balloon, catheter shaft, barrel, etc. The components of the various embodiments may be constructed from any of a wide variety of materials including polymers, metals etc.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims), hi jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A medical device, comprising:
   an elongate catheter shaft including a proximal region and a distal region, the distal region including an axle region, the axle region being longitudinally positioned between a first portion of the distal region and a second portion of the distal region, the first portion having a first diameter, the second portion having a second diameter, and the axle region having a third diameter, wherein the third diameter is less than the first diameter and the second diameter, the elongate catheter shaft defining an inflation lumen therethrough, wherein the axle region defines a fluid opening in fluid communication with the inflation lumen; and
   a rotatable assembly mounted about the axle region of the elongate catheter shaft, wherein the rotatable assembly is rotatable relative to the elongate catheter shaft, the rotatable assembly including a barrel and a balloon, the barrel being rotatable about the elongate catheter shaft and having an outer diameter that is substantially the same as at least one of the first diameter and the second diameter, the balloon disposed about the barrel, the balloon including a proximal waist bonded adjacent to a proximal end of the barrel and a distal waist bonded adjacent to a distal end of the barrel, the balloon being expandable between a reduced state and an expanded state, wherein the barrel defines at least one fluid port in fluid communication with an interior of the balloon, the at least one fluid port being in fluid communication with the inflation lumen via the fluid opening of the axle region.

2. The medical device of claim 1, wherein the barrel is mounted about the axle region to define a first gap between the barrel and the first portion of the distal region of the elongate catheter shaft and to define a second gap between the barrel and the second portion of the distal region of the elongate catheter shaft.

3. The medical device of claim 2, further comprising a first sealing mechanism and a second sealing mechanism, the first sealing mechanism positioned within the first gap, the second sealing mechanism positioned within the second gap.

4. The medical device of claim 3, wherein the balloon overlaps the first and/or second portion of the distal region of the elongate catheter shaft such that, during expansion of the balloon, the overlap forms a fluid tight seal between the barrel and the elongate catheter shaft.

5. The medical device of claim 1, wherein the balloon includes a body region defining a stent receiving region.

6. The medical device of claim 5, further comprising a stent, the stent having a reduced configuration and an expanded configuration, in the expanded configuration the stent having a diameter greater than that in the reduced configuration, in the reduced configuration the stent being disposed about the stent receiving region.

7. The medical device of claim 1, wherein the rotatable assembly includes a secondary guidewire housing defining a secondary guidewire lumen, the secondary guidewire housing engaged to a portion of the balloon.

8. The medical device of claim 7, wherein at least a portion of the secondary guidewire housing is bio-absorbable.

9. The medical device of claim 7, wherein at least a portion of the secondary guidewire housing is frangible.

10. The medical device of claim 7, wherein at least a portion of the secondary guidewire housing is defined by at least a portion of the barrel or balloon.

11. The medical device of claim 1, wherein the elongate catheter shaft defines a primary guidewire lumen for passage of a primary guidewire therethrough.

12. A medical device, comprising:
an elongate catheter shaft including a proximal region and a distal region, the distal region including an axle region, the axle region being longitudinally positioned between a first portion of the distal region and a second portion of the distal region, the first portion having a first diameter, the second portion having a second diameter, and the axle region having a third diameter, wherein the third diameter is less than the first diameter and the second diameter, the elongate catheter shaft defining an inflation lumen therethrough, wherein the axle region defines a first opening in fluid communication with the inflation lumen;
a barrel rotatably disposed about the axle region of the elongate shaft, the barrel defining a plurality of second openings in fluid communication with the first opening of the axle region; and
a balloon disposed about the barrel, the balloon being in fluid communication with the inflation lumen of the elongate catheter shaft via the first opening and the plurality of second openings.

13. The medical device of claim 12, wherein the balloon includes a proximal waist coupled to the barrel adjacent a proximal end of the barrel and a distal waist coupled to the barrel adjacent a distal end of the barrel.

14. The medical device of claim 12, wherein the barrel has a fourth diameter, the fourth diameter being substantially the same at least one of the first diameter and the third diameter.

15. The medical device of claim 12, wherein the barrel is mounted about the axle region to define a first gap between the barrel and the first portion of the distal region of the elongate catheter shaft and to define a second gap between the barrel and the second portion of the distal region of the elongate catheter shaft.

16. The medical device of claim 12, further comprising a secondary guidewire housing defining a secondary guidewire lumen, the secondary guidewire housing engaged to a portion of the balloon.

17. A medical device, comprising:
an elongate catheter shaft including a proximal region and a distal region, the distal region including an axle region, the axle region being longitudinally positioned between a first portion of the distal region and a second portion of the distal region, the first portion having a first diameter, the second portion having a second diameter, and the axle region having a third diameter, wherein the first diameter and the second diameter are substantially the same, wherein the third diameter is less than the first diameter and the second diameter, the elongate catheter shaft defining an inflation lumen therethrough, wherein the axle region defines a first opening in fluid communication with the inflation lumen, wherein the elongate catheter shaft defines a primary guidewire lumen for passage of a primary guidewire therethrough;
a tubular barrel rotatably disposed about the axle region of the elongate shaft, the tubular barrel defining a second opening in fluid communication with the first opening of the axle region, wherein the tubular barrel has a fourth diameter that is substantially the same as at least one of the first diameter and the third diameter;
a balloon disposed about the barrel, the balloon being in fluid communication with the inflation lumen of the elongate catheter shaft via the first opening and the second opening;
a secondary guidewire housing defining a secondary guidewire lumen, the secondary guidewire housing engaged to a portion of the balloon.

18. The medical device of claim 17, further comprising a stent disposed about at least a portion of the balloon and at least a portion of the secondary guidewire housing, the stent having a reduced configuration and an expanded configuration, in the expanded configuration the stent having a diameter greater than that in the reduced configuration, in the reduced configuration the stent being disposed about the stent receiving region.

* * * * *